United States Patent [19]

Spilburg et al.

[11] Patent Number: 4,720,486
[45] Date of Patent: Jan. 19, 1988

[54] METHOD OF INHIBITING VERTEBRATE COLLAGENASE ACTIVITY USING PEPTIDE HYDROXAMIC ACID DERIVATIVES

[75] Inventors: Curtis A. Spilburg, Chesterfield; William M. Moore, St. Charles, both of Mo.

[73] Assignee: Monsanto Company, St. Louis, Mo.

[21] Appl. No.: 1,265

[22] Filed: Jan. 7, 1987

Related U.S. Application Data

[62] Division of Ser. No. 789,271, Oct. 18, 1985, Pat. No. 4,687,841.

[51] Int. Cl.$^4$ .................... A61K 37/02; C08F 283/00
[52] U.S. Cl. ........................................ 514/18; 525/54.1
[58] Field of Search ........................... 514/18; 525/54.1

[56] References Cited

U.S. PATENT DOCUMENTS

| | | | |
|---|---|---|---|
| 3,931,184 | 1/1976 | Lex | 530/344 |
| 4,138,394 | 2/1979 | Sakakibara et al. | 530/328 |
| 4,443,367 | 4/1984 | Weingarten | 530/328 |
| 4,466,919 | 8/1984 | Weingarten | 530/329 |

OTHER PUBLICATIONS

Masui et al., Biochem. Med., 17, 215–221, (1977).
Nishino and Powers, Biochem., 17, 2846, (1978).
Nishino and Powers, Biochem., 18, 4340–4347, (1979).

*Primary Examiner*—Delbert R. Phillips
*Assistant Examiner*—Nathan M. Nutter
*Attorney, Agent, or Firm*—Scott J. Meyer; James W. Williams, Jr.

[57] ABSTRACT

Novel peptide hydroxamic acid derivatives having useful collagenase inhibitory activity and capable of forming affinity resins for the purification of vertebrate collagenase are defined by the following structural formula:

R—Pro—Leu—Gly—NHOH wherein R=H or N-protecting group or agarose.

4 Claims, 2 Drawing Figures

METHOD OF INHIBITING VERTEBRATE COLLAGENASE ACTIVITY USING PEPTIDE HYDROXAMIC ACID DERIVATIVES

This is a division of application Ser. No. 789,271, filed Oct. 18, 1985, and now U.S. Pat. No. 4,687,841.

BACKGROUND OF THE INVENTION

This invention relates to novel peptide hydoxamic acid derivatives having useful collagenase inhibitory activity and capable of forming affinity resins for the purification of vertebrate collagenase.

Collagenase is a highly specific, neutral protease which cleaves undenatured collagen at a point about three quarters the distance from the amino terminal end. The enzyme plays a critical role in a variety of normal and pathological states such as resorption of the postpartum uterus, wound healing, rheumatoid arthritis and tumor invasion. Thus, in arthritic and arthrosic diseases, synovial collagenase plays a prominent role in the degradation of the main macromolecules of cartilage, collagen and proteoglycans, since once the collagen fibers of the cartilage are destroyed, joint destruction is irreversible. Accordingly, a specific collagenase inhibitor would be considered as a potential therapeutic agent for use against cartilage destruction in rheumatic diseases. Methods for purification of vertebrate collagenase are useful for the study of the role of collagenase in these and other such pathological conditions.

BRIEF DESCRIPTION OF THE INVENTION

In accordance with the present invention, certain novel peptide hydroxamic acid derivatives have been found to have useful collagenase inhibitory activity and are capable of forming affinity resins for the purification of vertebrate collagenase. These peptide derivatives are defined by the following structural formula:

R—Pro—Leu—Gly—NHOH wherein R=H or N-protecting group or agarose.

In the peptide structures shown herein, the amino acid components are designated by conventional abbreviations as follows:

| Amino Acid | Abbreviated Designation |
|---|---|
| L-Alanine | Ala |
| Glycine | Gly |
| L-Leucine | Leu |
| L-Methionine | Met |
| L-Phenylalanine | Phe |

The N-protecting group depicted as R in the above structural formula can be any group which will block α-amino functions and, preferably, is alkanoyl, aroyl and cycloalkanoyl. Most preferably, the blocking group is acetyl, benzoyl, carbobenzyloxy (Z) or t-butyloxycarbonyl (t-BOC).

For use as an affinity resin, R is preferably agarose. Agarose is a naturally occurring linear polysaccharide of galactose and 3,6-anhydrogalactose. A large variety of agaroses and modified agaroses are available commercially which can be used in accordance with the invention.

The novel peptide hydroxamic acid derivatives of this invention have been found to be effective inhibitors of collagenase from human synovial cells and human skin fibroblast cells. Thus, the N-protected R—Pro—Leu—Gly—NHOH is about ten times more active than the close analog R—Leu—Leu—Gly—NHOH. It is also a much more potent collagenase inhibitor than the analogous thiopeptolide Ac—Pro—Leu—Gly—S—Leu—Leu—Gly—OC$_2$H$_5$ described in application Ser. No. 571,227, filed Jan. 16, 1984 and now U.S. Pat. No. 4,569,907 and assigned to a common assignee. Moreover, it is estimated to be about 50-100 times more active than a commercially available collagenase inhibitor product (Zincov) which chemically is 2-(N-Hydroxycarboxamido)-4-methylpentanoyl-L-Alaglycine amide.

When the N-protecting group (or blocking group) is removed (that is, when R=H) and the peptide hydroxamic acid is covalently bound to agarose, a highly effective affinity resin is obtained. The affinity resin is useful for the purification of large quantities of human collegenase. By use of the affinity resin, skin fibroblast collagenase was purified over 500 fold in 76% yield using this single purification step. When assayed by polyacrylamide gel electrophoresis with sodium dodecyl sulfate (SDS) and visualized in the presence of mercaptoethanol, active collagenase isolated by this method consisted of two bands, a major species with molecular weight 45,000 and a minor one with molecular weight 50,000. When the affinity-purified material was passed over an Ultrogel AcA 44 gel exclusion column, a molecular weight of 45,000 was found, indicating the absence of sulfhydryl-linked subunits. Ultrogel AcA 44 consists of spherical beads of agarose trapped within a cross-linked polyacrylamide gel and is commercially available from LKB, Bromma, Sweden.

The affinity column also was able to isolate collagenase from human synovial cells. The major purification occurs at the affinity column step, but an additional gel filtration step was occasionally required to achieve complete purification. The molecular weight and amino acid composition of this synovial enzyme agree closely with those of the skin enzyme; however, in this case, only a single species of molecular weight 45,000 was found.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in connection with the accompanying drawings in which:

Figure 1:
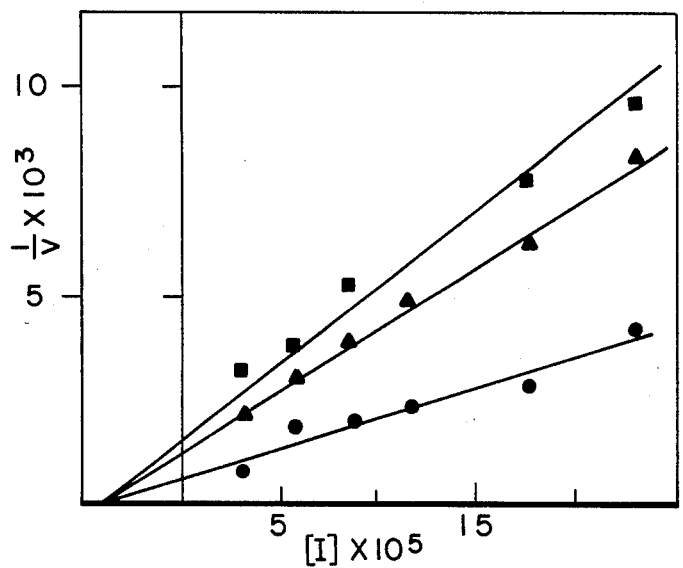
FIG. 1 is a plot of the inhibition of human synovial collagenase by the peptide hydroxamic acid derivative in one embodiment of the invention, at 3.9 μM collagen ( ● ), 1.3 μM collagen ( ▲ ) and 0.7 μM collagen ( ■ ).

The peptide hydroxamic acid derivatives of this invention can be prepared by classical methods of peptide synthesis followed by conversion of the peptide to the hydroxamic acid derivative. Thus, the tripeptide moiety can be prepared by a series of coupling reactions in which the constituent amino acids are linked together by peptide bonds in the desired sequence. Commercially available N-protected-L-proline also can be coupled with the commercially available dipeptide L-leucylglycine. Activated esters of N-hydroxysuccinimide are useful in this peptide synthesis by procedure described by Anderson et al., *J. Amer. Chem. Soc.* 86, 1839-1842 (1964). According to this procedure, dicyclohexycarbodiimide ($C_6H_{11}N=C=NC_6H_{11}$) (DCC) is used to form the activated ester.

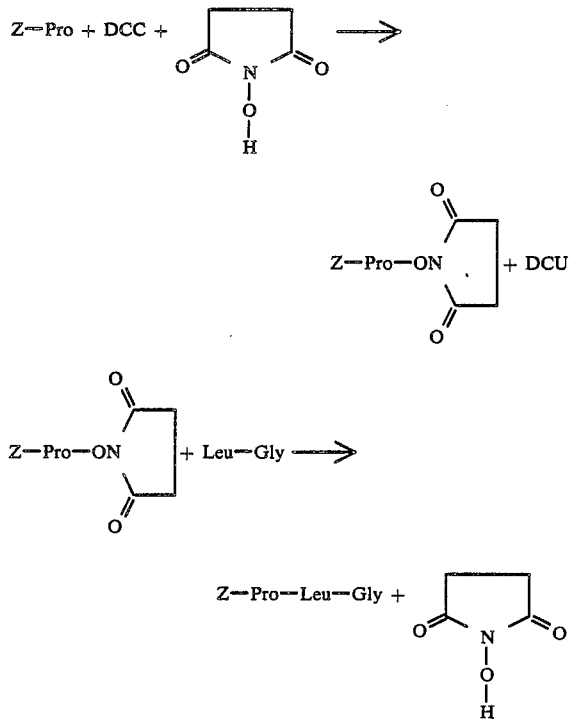

Z—Pro—Leu—Gly is analogously converted to the active ester and then reacted with hydroxylamine to form Z—Pro—Leu—Gly—NHOH.

According to a preferred method, the peptide hydroxamic acid derivatives of this invention can be prepared by the following series of steps:

I. Form the N-hydroxysuccinimide ester of the N-protected-L-proline, e.g., t—BOC—proline or Z-proline, by reaction with N,N-dicyclohexylcarbodiimide and N-hydroxysuccinimide in about equimolar proportions.

II. Couple the resulting N-hydroxysuccinimide ester by reaction with the dipeptide L-leucylglycine in about equimolar proportions.

III. React the resulting t—BOC— or Z—Pro—Leu—Gly with N,N-dicyclohexylcarbodiimide and N-hydroxysuccinimide in about equimolar proportions.

IV. React the resulting N-hydroxysuccinimide ester with hydroxylamine to form the hydroxamic acid derivative of the peptide.

The reactions with DCC and N-hydroxysuccinimide are preferably carried out in dioxane solutions. The formed dicyclohexylurea (DCU) can be removed by filtration and the solvent removed by stripping under reduced pressure. The remaining desired activated esters can be recovered by crystallization.

Reaction II is conveniently carried out by dissolving the activated ester of t—BOC—Pro or Z—Pro in dioxane solvent and adding to an aqueous solution of Leu—Gly containing $NaHCO_3$. Following completion of the reaction, the solvent is removed by acidifying and stripping under reduced pressure.

The hydroxylamine solution for reaction IV is readily prepared by dissolving solid hydroxylamine.HCl in dimethylformamide (DMF) solvent, adding about an equimolar amount of triethylamine and filtering off the hydrochloride salt. The remaining solution is then mixed with the solution of the active ester of the peptide from reaction III to form a solution of the hydroxamic acid derivative of the peptide. The resulting solution is then neutralized and the solvent is removed by evaporation to leave the desired solid peptide hydroxamic acid derivative.

The affinity resin of the peptide hydroxamic acid derivative of this invention can be prepared by removing the t—BOC, Z or other blocking group and then coupling the unblocked peptide hydroxamic acid derivative to agarose. A preferred method comprises coupling the unblocked Pro—Leu—Gly—NHOH to activated CH-Sepharose ® 4B which is commercially available from Pharmacia Fine Chemicals AB, Uppsala, Sweden. This material provides a six-carbon spacer arm and an active ester for spontaneous coupling via amino groups. The initial step of unblocking can be readily carried out by treatment with anhydrous HF.

The following examples will further illustrate the invention although it will be understood that the invention is not limited to these specific examples.

EXAMPLE 1

Preparation of N-Benzyloxycarbonyl-L-prolyl-L-leucylglycine Hydroxamic Acid (Z—Pro—Leu—Gly—NHOH).

Compounds were characterized by amino acid analysis after acid hydrolysis, TLC (Silica Gel 60 F-254; $CHCl_3:CH_3OH::3:1$), melting point, IR (1% KBr pellets) and extinction coefficient of the corresponding $Fe^{3+}$ complex at 540 mμ (50 μl of 10 mg/ml solution in dimethylformamide added to 3.0 ml of 2% $FeCl_3$ in 0.10 N HCl).

N-Benzyloxycarbonyl-L-proline succinimide ester (Z—Pro—OSu) was prepared as follows:

Z—Pro (7.5 gm, 0.03 mole) and N-Hydroxysuccinimide (3.45 gm, 0.03 mole) were dissolved in cold dioxane and dicyclohexylcarbodiimide (DCC) (6.18 gm, 0.03 mole) was added with rapid stirring. The mixture was stirred overnight at room temperature and the next day the solid dicyclohexylurea (DCU) was filtered off. The solvent was removed and the oil was recrystallized from isopropyl alcohol. Crystals of Z—Pro—OSu formed with scratching. Yield 8.4 gm. Melting point 86.5°-87.5° C.

Z—Pro—OSu (3.46 gm, 10 mmol) as prepared above was dissolved in dioxane and added to an aqueous solution of Leu—Gly (1.88 gm, 10 mmol) containing sodium bicarbonate (1.68 gm, 20 mmol). The solution was stirred overnight at room temperature, acidified to pH 2.0 and all the solvent was removed under reduced pressure. The remaining solid Z—Pro—Leu—Gly was washed with water and recrystallized from ethanol-water. Yield 3.2 gm. Melting point 165.5-166. In a clean, dry breaker, Z—Pro—Leu—Gly (2.72 gm, 6.5 mmol) and N-hydroxysuccinimide (0.98 gm, 6.5 mmol) were dissolved in 25 ml dioxane, and dicyclohexylcarbodiimide (DCC) (1.34 gm, 6.5 mmol) was added with stirring. The solution was stirred overnight, and the following day the resulting solid dicyclohexylurea (DCU) was filtered off and the remaining solution was retained. A separate solution of hydroxylamine (0.68 gm, 9.75 mmol) was prepared by dissolving hydroxylamine HCl in 10 ml dimethylformamide (DMF) and adding triethylamine (1.34 ml, 9.75 mmol). After filtering off the hydrochloride salt, the two solutions were mixed and stirred overnight at room temperature. The next day the solution was neutralized, the solvent was removed on the rotovap and the solid Z—Pro—Leu—Gly—NHOH was recrystallized from ethanol-water. Yield 1.3 gm. Melting point 141-143. $R_f=0.63$. Amino Acid Analysis: Gly 1.00; Leu 1.04; Pro 0.95. $\epsilon_{540}=910$.

EXAMPLE 2

Several other hydroxamic acid compounds were prepared for comparison (Table I, below) with the Z—Pro—Leu—Gly—NHOH of Example 1. These hydroxamic acid compounds were synthesized by the nucleophilic attack of hydroxylamine on either peptide methyl esters or succinimide esters. Compounds were characterized by amino acid analysis after acid hydrolysis, TLC (Silica Gel 60 F-254; $CHCl_3:CH_3OH::3:1$), melting point, IR (1% KBr pellets) and extinction coefficient of the corresponding $Fe^{3+}$ complex at 540 m$\mu$ (50 $\mu$l of 10 mg/ml solution in DMF added to 3.0 ml of 2% $FeCl_3$ in 0.10 N HCl).

METHOD A

In a clean, dry beaker, 1.6 gm (5 mmol) Z—Leu—Gly (Sigma) and 0.75 gm (5 mmol) N-hydroxysuccinimide were dissolved in 25 ml dioxane, and 1.03 gm (5 mmol) DCC was added with stirring. The solution was stirred overnight, and the following day the solid DCU was filtered off. A solution of hydroxylamine was prepared by dissolving 0.52 gm $NH_2OH \cdot HCl$ (7.5 mmol) in 10 ml DMF and adding 1.03 ml (7.5 mmol) triethylamine. After filtering off the hydrochloride salt, the two solutions were mixed and stirred overnight at room temperature. The next day the solution was neutralized, the solvent was removed on the rotovap and the remaining solid was recrystallized from ethyl acetate-hexane. The oil was collected and triturated with ether. Yield 500 mg. Melting point 110-113. Amino acid analysis: Gly 1.00; Leu 1.03. $R_f=0.80$. $\epsilon_{540}=890$.

METHOD B

In a small beaker, 0.34 gm (4.8 mmol) $NH_2OH \cdot HCl$ was dissolved in 0.75 ml $H_2O$ and 0.60 ml ethanol. When all the solid dissolved, the solution was placed in an ice bath, and 1 ml of 10N KOH (10 mmol) was added dropwise with stirring. The ice was removed and the mixture was added to a solution of 1.4 gm (4.8 mmol) Z—Ala—Gly—OMe (Sigma) in 30 ml of methanol. The solution was stirred for one hour at room temperature and the pH lowered to below 7 by the dropwise addition of concentrated HCl. The beaker was cooled on ice, the salt was filtered off and then all the solvent was removed on the rotovap. This solid was taken up in water and extracted with ethyl acetate. The water layer was evaporated on the rotovap and the solid was recrystallized from ethyl acetate. Yield 400 mg. Melting point 144.5-146.5. Amino acid analysis: Gly 1.00; Ala 0.98. $R_f=0.70$, $\epsilon_{540}=890$.

Z—Gly—NHOH

This compound was prepared from Z—Gly (4.2 gm, 20 mmol) using Method A. After the hydroxamic acid was neutralized with acid, the solvent was removed and the solid was recrystallized from hot water. Yield 2.2 gm. Melting point 120.5-122. $R_f=0.74$, $\epsilon_{540}=940$.

Z—Gly—GLY—NHOH

This compound was prepared from Z—Gly—Gly (2.66 gm, 10 mmol) using Method A and recrystallized from boiling water. Yield 1.6 gm. Melting point 150-151.5. $R_f=0.58$, $\epsilon_{540}=900$.

Z—Phe—Gly—NHOH

Z—Phe (3.0 gm, 10 mmol) and N-hydroxysuccinimide (1.15 gm, 10 mmol) were dissolved in 40 ml cold DMF, and DCC (2.06 gm, 10 mmol) was added with rapid stirring. The solution was stirred for one hour on ice and then overnight at room temperature. The next day the solid DCU was filtered off and the clear solution was added to an aqueous solution of glycine methyl ester, prepared by dissolving the hydrochloride salt (1.78 gm, 11 mmol) in water containing $NaHCO_3$ (1.85 gm, 22 mmol). The mixture was stirred for two hours at room temperature, the pH was adjusted to 2, the solvent was removed and the remaining solid was taken up in ethyl acetate. The solution was extracted with water, the organic layer was dried over $MgSO_4$ and the peptide was crystallized by adding hexane to the boiling ethyl acetate solution. Yield 3.0 gm. Melting pt. 116.5-118. $R_f=0.94$. Amino acid analysis: Gly 1.00; Phe 1.01. The hydroxamate was prepared from the ester (2.1 gm, 5 mmol) using Method B. The crude solid was taken up in ethyl acetate and recrystallized from ethyl acetate-hexane. Yield 1.0 gm. Melting point 148-150. $R_f=0.82$. Amino acid analysis: Gly 1.00; Phe 1.02. $\epsilon_{540}=1013$.

Z—Met—Gly—NHOH

This compound was prepared from Z—Met—Gly—OEt (Sigma - 2.76 gm, 7.5 mmol) using Method B. The crude solid was extracted with ethyl acetate and recrystallized from ethyl acetate. Yield 1.0 gm. Melting point 133-134. $R_f=0.76$. Amino acid analysis Gly 1.00; Met 0.73 (starting material Gly 1.00; Met 0.60). $\epsilon_{540}=870$.

Z—Leu—Leu—Gly—NHOH

Z—Leu (2.7 gm, 10 mmol) and N-hydroxysuccinimide (1.15 gm, 10 mM) were dissolved in dioxane, and DCC (2.06 gm, 10 mmol) was added with rapid stirring on ice. The solution was stirred overnight at room temperature, and the next day the solid DCU was filtered off. The clear solution was added to an aqueous solution of Leu—Gly (Sigma - 2.07 gm, 11 mmol) prepared by adding the solid Leu—Gly to $NaHCO_3$ (1.85 gm, 22 mmol) dissolved in water. The mixture was stirred for four hours at room temperature, the solution was adjusted to pH 2 by adding concentrated HCl and all the solvent was removed on the rotovap. The gummy mass was dissolved in ethyl acetate, extracted with water and the organic layer was dried over $MgSO_4$. The peptide was recrystallized from ethyl acetate-hexane; the oil which formed was collected and crystallized by triturating with ether. Yield 2.1 gm. Melting point 96.5-99.5. The hydroxamate was prepared from Z—Leu—Leu—Gly (1.8 gm, 4.1 mmol) using Method A. Yield 0.9 gm. Melting point 113-116. Amino acid analysis: Gly 1.00; Leu 2.04. $R_f=0.81$. $\epsilon_{540}=930$.

EXAMPLE 3

Preparation of Collagenase Affinity Column.

Five hundred milligrams of Z—Pro—Leu—Gly—N-HOH as prepared in Example 1 were treated with anhydrous HF to remove the carbobenzyloxy blocking group. The unblocked peptide was dissolved in water and extracted two times with chloroform, once with hexane and the aqueous layer was lyophilized. Prolylleucylglycyl hydroxamic acid was coupled to activated CH-Sepharose 4B according to the manufacturer's recommended general procedure for coupling Sepharose. (Pharmacia Fine Chemicals AB, Uppsala, Sweden). Specifically, the freeze dried resin (15 gm) was swollen and washed with 3 liters of 1 mM HCl on a sintered glass funnel to give 45 ml of gel with a capacity of 5-7 μmole/ml. The unblocked peptide (180 mg) was dissolved in 45 ml of 0.10M sodium bicarbonate, pH 8.0, and mixed with the gel for 60 minutes at 23° C. The coupled gel was then washed with 0.10M Tris, 0.50M NaCl, pH 8.0, alternating with 0.10M sodium acetate, 0.50M NaCl, pH 4.0, and stored at 4° in 0.05M Tris, 0.50M NaCl, 0.01M $CaCl_2$, pH 7.5. A 0.50 ml aliquot of the gel was hydrolyzed in 6N HCl and found to contain 2.5 μmole each of Pro, Leu and Gly.

EXAMPLE 4

Collagenase Inhibition Tests

The peptide hydroxamic acid derivatives prepared according to Example 1 and 2, above were tested for their activity as inhibitors of collagenase as follows:

$^{14}C$-Collagen $^{14}C$-collagen was prepared by reductive methylation of calf skin collagen at 4° C. using $^{14}C$-formaldehyde and sodium borohydride. Calf skin collagen (Sigma) was dissolved at 7.5 mg/ml in 60 ml of 0.10M acetic acid and dialyzed at 4° C. against 0.15M potassium phosphate, pH 7.6, for eight hours followed by dialysis overnight against 0.4M NaCl. The collagen solution was then adjusted to pH 9.0 by addition of 0.50M sodium borate and then 1 mCi of $^{14}C$-formaldehyde (10 mCi/mmol) was added. After one minute, 0.10M sodium borohydride (660 μl in 1.3 mM NaOH) was added in four aliquots, followed by an additional aliquot (340 μl) 30 minutes later. The solution was then dialyzed exhaustively against 0.01M acetic acid, centrifuged to remove particulates and stored frozen in 1 ml aliquots. Specific activity was $1.3 \times 10^6$ DPM/mg. Unlabeled collagen was prepared in the same way, stored frozen and mixed with labeled collagen at a ratio of 9 to 1. For assay, the diluted $^{14}C$-collagen was dialyzed 6-8 hours at 4° C. against 0.15M potassium phosphate, pH 7.6, followed by dialysis overnight against 0.4M sodium chloride. This solution was centrifuged to remove any undissolved collagen and stored at 4° C.

Enzyme Assays

Collagenase asays were carried out according to the method of Terato et al., *Biochim. Biophys. Acta* 445, 753 (1976). They were performed in 1.5 ml polypropylene microfuge tubes. Each assay tube contained 50 μl of $^{14}C$-collagen solution (4 mg/ml) and 50 μl of 1.0M glucose, 0.10M Tris, 0.4M NaCl, 0.02M $CaCl_2$, pH 7.5. This solution was incubated for ten minutes at 35° C. and the reaction initiated by the addition of 100 μl of enzyme solution. Those samples containing procollagenase were first activated by incubating 100 μl aliquots with 1-5 μl of 10 mg/ml trypsin (in 1 mM HCl) for 20 minutes at 23° C., followed by 20 μl of 5 mg/ml soybean trypsin inhibitor (in 0.05M Tris, 0.01M $CaCl_2$, pH 7.5) to quench the trypsin activity. The collagenase assay was terminated after 30 minutes at 35° C. by the addition of 20 μl of 0.08M 1,10-phenanthroline in 50% (v/v) dioxane and the incubation was continued for one hour at 35° C. to denature the collagen digestion products. Each sample was cooled for 15 minutes at 23° and 200 μl of dioxane was added with vigorous vortexing to precipitate uncleaved collagen. Following centrifugation at 11,000 RPM, 350 μl aliquots were added to 5.0 ml of Pico-Fluor 30 to determine radioactivity.

Collagenase Inhibition

Collagenase activities were measured in the presence of the test compounds by adding an aliquot of the compound (0–85 μl) and buffer to 100 μl of glucose-collagen solution to give a total volume of 185 μl, incubating at 35° C. for 10 minutes and then initiating the reaction with 15 μl of purified collagenase. The rest of the assay was performed as described above.

To determine the mechanism of inhibition, the following equation was used [(Holmquist and Vallee, *J. Biol. Chem.* 249, 4601 (1974)]

$$\log\left(\frac{A_o}{A_I} - 1\right) = \log K_I + n \log I$$

where $A_o$ is the activity in the absence of inhibitor and $A_I$ is the activity in the presence of inhibitor.

SK Hepatoma Cells

One vial of frozen SK Hepatoma cells (American Type Cell Culture HTB-52) was rapidly thawed in a 37° C. water bath, the contents were transferred to a 75 $cm^2$ T-flask and 25 ml of Dulbecco's modified Eagle's medium (DMEM) containing 10% fetal bovine serum (FBS) was added. The flask was incubated at 37° C. in an atmosphere containing 6-8% $CO_2$. After one day, the media was changed to remove the last traces of the freezing media and four days later the cells were washed with 25 ml phosphate buffered saline (PBS) containing 0.02% EDTA (ethylenediamine tetraacetate). Five ml of the same media were added and the cells were removed with gentle tapping. Five 75 $cm^2$ T-flasks were inoculated with 1 ml of cells and 25 ml of DMEM containing 10% FBS were added. For suspension culture, a 500 ml spinner flask was inoculated with cells from five 75 $cm^2$ T-flasks and sufficient DMEM containing 10% FBS was added to bring the volume to 500 ml. The spinner was maintained in a $CO_2$ incubator at 37° C. with 6-8% $CO_2$. The media was harvested three times per week by pouring off 400-450 ml and leaving 50-100 ml for reinoculation. Cells were removed by centrifugation and the conditioned media was sterile filtered and used to treat fibroblast and synovial cells.

Skin Fibroblast Cells

One vial of normal skin fibroblasts was purchased (American Type Cell Culture CRL 1224), thawed at 37° C. and transferred to a 150 $cm^2$ T-flask. Fifty ml of DMEM containing 10% FBS were added and the cells incubated for one week at 37° C. under 5% $CO_2$. The cells were then split into three T-flasks. When the flasks became overgrown with cells, normal media was replaced with SK Hepatoma conditioned media and changed twice a week. This media was stored and used as the starting material for collagenase isolation.

Isolation and Culture of Synovial Cells

Approximately 2.0 gms of synovial tissue were obtained from a patient undergoing synovectomy of the knee. All procedures were carried out in a laminar flow hood under aseptic conditions. The tissue was placed in 250 ml McCoys 5A (modified) medium containing 200 μg/ml gentamicin and stored overnight at 0° C. The next day the tissue was warmed to room temperature, cut into 0.25 cm pieces and added to 11 ml of serum-free DMEM, containing 4 mg/ml clostridial collagenase (Worthington). After incubating the mixture for one hour at room temperature, an equal volume of 0.25% trypsin was added and the incubation continued for an additional thirty minutes. The cells were spun down at 400×g for ten minutes, resuspended in 20 ml trypsin-/EDTA (Gibco 10×) and incubated for 30 minutes with occasional mixing by drawing through a 25 ml pipet. The suspension was centrifuged and the pellet was washed two times with PBS:DMEM (1:1) containing 10% FBS. The cells were resuspended at $1 \times 10^6$ cells/ml in DMEM containing 10% FBS and 100 μg gentamicin. After incubating overnight at 37° in a $CO_2$ incubator (5-8% $CO_2$), the non-adherent cells were aspirated off and the adherent cells were washed with PBS:DMEM (1:1) containing 10% FBS, followed by DMEM containing only 10% FBS. At the first passage, the original T-flask was split one to four. As described above, when the cells became confluent, 30% SK Hepatoma conditioned media was added to the T-flask to stimulate the cells to produce collagenase. This was the starting material for enzyme isolation.

To determine the $K_I$ values of the peptide hydroxamic acid derivatives tested for collagenase inhibition, the inhibition by Z—Pro—Leu—Gly—NHOH was measured over a ten-fold concentration range at three different substrate concentrations, 3.9 μM, 1.3 μM and 0.7 μM and the data plotted as a Dixon plot. All the plots were linear and intersected on the abscissa, $-K_I$, indicating non-competitive inhibition as seen from FIG. 1. The other test compounds were assumed to inhibit by the same mechanism so that all studies were performed at only a single substrate concentration, 10μM, and the $K_I$ values were determined from the intersection with the abscissa.

Table I, below, sets forth the $K_I$ values of these peptide hydroxamic acid derivatives when thus tested for inhibition of human collagenase as above isolated from skin fibroblasts and synovial cells. With a $K_I$ of $4 \times 10^{-5}$M, the Z—Pro—Leu—Gly—HNOH was found to be ten times more effective than the corresponding Z—Leu—Leu—Gly—NHOH analog and, moreover, this was the most effective inhibitor among the compounds tested. It is also estimated to be about 50 to 100 times more active than Zincov which has a $K_I$ of $2 \times 10^{-3}$M.

TABLE I $K_I$ VALUES OF PEPTIDE HYDROXAMIC ACID INHIBITORS OF COLLAGENASE[a]

| TEST INHIBITOR | $K_I$(mM) SYNOVIAL COLLAGENASE | FIBROBLAST COLLAGENASE |
|---|---|---|
| Z—Gly—NHOH | 0.96 | 0.60 |
| Gly—NHOH | 18. | >1 |
| Z—Gly—Gly—NHOH | 2.0 | 3.0 |
| Z—Ala—Gly—NHOH | 2.6 | 1.3 |
| Z—Leu—Gly—NHOH | 0.17 | 0.48 |
| Z—Phe—Gly—NHOH | 0.10 | 0.15 |
| Z—Met—Gly—NHOH | 0.20 | 0.15 |
| Z—Leu—Leu—Gly—NHOH | 0.33 | 0.30 |
| Z—Pro—Leu—Gly—NHOH | 0.047 | 0.040 |

[a]0.50 M NaCl, 0.01 M $CaCl_2$, 0.05 M Tris, pH 7.5, 35° C.

EXAMPLE 5

Purification of Collagenase

Figure 2:
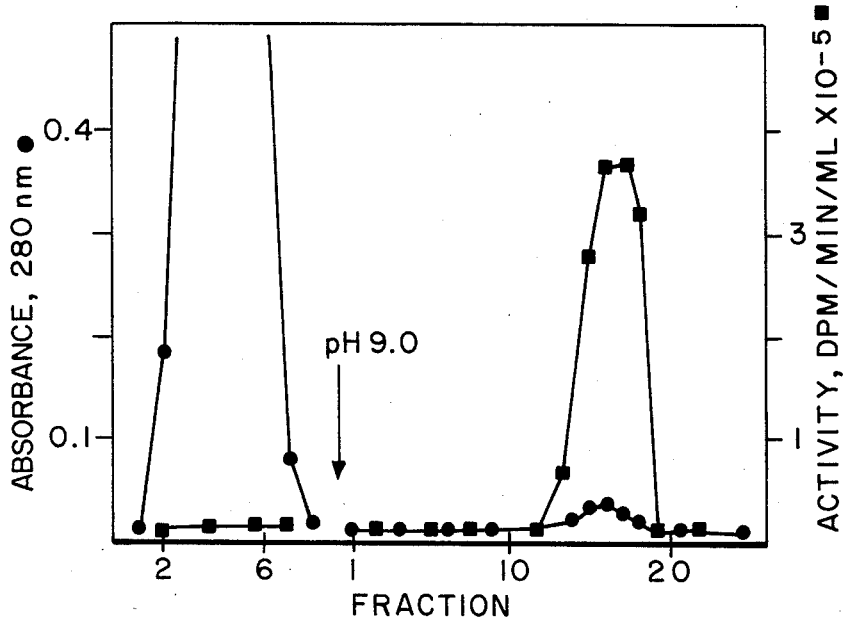
FIG. 2 shows the affinity chromatographic profile of human skin collagenase using an affinity column of Pro—Leu—Gly—NHOH covalently bound to agarose.

The Affinity matrix prepared by coupling Pro—Leu—Gly—NHOH to agarose according to Example 3 was used to purify collagenase as follows. In a typical test, 100 ml of SK Hepatoma media were removed from either skin fibroblasts or synovial fibroblasts and treated with ammonium sulfate to 55% of saturation. The precipitate was collected by centrifugation, dissolved in water and then dialyzed against 0.50M NaCl, 0.01M $CaCl_2$, 0.01M Tris, pH 7.5. Most cells produce collagenase as an inactive zymogen or as an enzyme inhibitor complex so that no activity is observed in the starting cell culture media. However, when this same media is treated with trypsin, collagenase activity is generated. Therefore, the dialyzed protein solution was made one mg/ml in tryspin, allowed to stand at room temperature for twenty minutes and then solid soybean trypsin inhibitor was added to give a final concentration of 1.5 mg/ml. The mixture was then pumped onto the affinity column (1.5×15 cm) at 15 ml/hr and the column was washed with 0.50M NaCl, 0.01M $CaCl_2$, 0.01M Tris, pH 7.5. As shown in FIG. 2, most of the protein washed through the column and all the activity was bound. When the protein absorbance returned to zero, the column was washed with 0.50M NaCl, 0.10M $CaCl_2$, 0.10M Tris, pH 9.0. Since collagenase has lower stability at high pH, 2.5 ml fractions were collected into one ml of 0.50M NaCl, 0.60M Tris, pH 6.5. Under these conditions, all the activity was eluted in a single protein peak (FIG. 2). For the skin enzyme, when the three or four peak fractions were pooled and examined by polyacrylamide gel electrophoresis with sodium dodecyl sulfate (SDS), one major band and a faint minor band were found at molecular weight 45,000 and 50,000 respectively, indicating that the enzyme was essentially pure. For the synovial enzyme there were still some impurities remaining after this affinity step so that an additional gel exclusion column was required for complete purification. An AcA 44 gel exclusion column was used for this purpose. When the active fractions from this column were pooled and examined on SDS gels, a single band of molecular weight 45,000 was found. The purification scheme for both enzymes is summarized in Table II and, as shown there, both can be isolated in high yield and with high specific activity. Importantly, when either of these enzymes was incubated with collagen and the cleavage products visualized on SDS gels, only the characteristic ¾-¼ collagen cleavage products were observed.

After each run, the column was regenerated by washing with 0.05M EDTA, 0.50M NaCl, pH 7.5, followed by 0.50M NaCl, 0.01M CaCl$_2$, 0.01M Tris, pH 7.5. One column was used over 25 times over a period of six months, with no apparent loss of capacity or other chromatographic properties.

Trypsin activation was essential for the isolation of either enzyme. When media was treated with ammonium sulfate as described above and then pumped onto the column with no trypsin activation, no protein was eluted with pH 9.0 buffer. However, if each fraction of the unbound material was activated with trypsin for 20 minutes and this exogenous activity quenched with soybean inhibitor, all the collagenase activity was found in the column wash through, indicating that the inactive enzyme was not bound to the resin.

Various other examples will be apparent to the person skilled in the art after reading the present disclosure without departing from the spirit and scope of the invention and it is intended that all such examples be included within the scope of the appended claims.

What is claimed is:

1. A method of inhibiting vertebrate collagenase activity comprising treating a vertebrate collagenase-containing substrate with a collagenase inhibitory effective amount of a peptide hydroxamic acid derivative having the following structural formula:

R—Pro—Leu—Gly—NHOH wherein R=H or N-protecting group or agarose.

2. The method of claim 1 in which the collagenase-containing substrate is human synovial collagenase.

3. The method of claim 1 in which the collagenase-containing substrate is human skin fibroblast collagenase.

4. A method of isolating vertebrate collagenase comprising treating a vertebrate collagenase-containing substrate with an affinity resin comprising agarose covalently coupled to the peptide hydroxamic acid derivative Pro—Leu—Gly—NHOH.

TABLE II

| | PURIFICATION OF HUMAN COLLAGENASES | | | | | | | | | |
|---|---|---|---|---|---|---|---|---|---|---|
| | SKIN | | | | | SYNOVIAL | | | | |
| Step | Protein ($A_{280}$) | Total Activity[a] $\times 10^{-3}$ | Sp. Act. (U/$A_{280}$) $\times 10^{-3}$ | Recovery % | Purification (-fold) | Protein ($A_{280}$) | Total Activity[a] $\times 10^{-3}$ | Sp. Act. (U/$A_{280}$) $\times 10^{-3}$ | Recovery % | Purification (-fold) |
| Media | 432 | 8450 | 20 | 100 | 1 | 3486 | 5890 | 1.7 | 100 | 1 |
| Amonium Sulfate | 92 | 6290 | 68 | 74 | 3.4 | 869 | 2051 | 2.4 | 35 | 1.4 |
| Affinity | 0.63 | 6600 | 10600 | 76 | 530 | 1 | 3484 | 3484 | 59 | 2050 |
| AcA 44 | | | | | | 0.42 | 4200 | 10000 | 71 | 5880 |

[a]Activity expressed as DPM/min.